United States Patent
Shiba et al.

(10) Patent No.: US 6,781,020 B2
(45) Date of Patent: Aug. 24, 2004

(54) WATER SOLUBLE BACTERICIDE AND PRODUCING METHOD THEREOF

(75) Inventors: Akihiko Shiba, Tokyo (JP); Kiyoko Shiba, Tokyo (JP); Gotaro Shiota, Tokyo (JP); Yoshiaki Maruyama, Tokyo (JP)

(73) Assignee: VMC Co., Ltd., Tokyo (JP)

( * ) Notice: Subject to any disclaimer, the term of this patent is extended or adjusted under 35 U.S.C. 154(b) by 0 days.

(21) Appl. No.: 10/215,999

(22) Filed: Aug. 8, 2002

(65) Prior Publication Data

US 2003/0032668 A1 Feb. 13, 2003

(30) Foreign Application Priority Data

Aug. 10, 2001 (JP) ........................................ 2001-243083

(51) Int. Cl.$^7$ ......................... C07C 29/00; C07C 31/00; C07C 31/02; C07C 33/00; C07C 27/10
(52) U.S. Cl. .................... 568/909.8; 568/902; 568/910; 568/910.5; 568/840; 568/852
(58) Field of Search .............................. 568/909.8, 902, 568/910, 840, 852, 910.5

(56) References Cited

U.S. PATENT DOCUMENTS 5,501,845 A * 3/1996 Duarte .................. 422/186.19

FOREIGN PATENT DOCUMENTS

DE 6343323 A1 * 6/1988

* cited by examiner

Primary Examiner—Johann Richter
Assistant Examiner—Elvis O. Price
(74) Attorney, Agent, or Firm—Bachman & LaPointe, P.C.

(57) ABSTRACT

A water soluble bactericide is obtained by ozone-oxidizing glycerin. Specifically, a 0.1 to 20% glycerin aqueous solution and gas phase ozone obtained by ozonizing oxygen through contact between oxygen and a silent discharge field, are brought into gas-liquid contact with each other, thereby to ozone-oxdize glycerin. Alternatively, a 0.1 to 20% glycerin aqueous solution is electrolyzed, thereby to produce ozone directly in the glycerin aqueous solution.

1 Claim, 11 Drawing Sheets

0.03% HYDROGEN PEROXIDE

OZONE-OXIDIZED GLYCERINE

10% GLYCERINE

1 UNIT CORRESPONDS TO 1PPM OZONE

WATER SOLUBLE BACTERICIDE AND PRODUCING METHOD THEREOF

CROSS-REFERENCE TO RELATED APPLICATIONS

This application is based upon and claims the benefit of priority from, the prior Japanese Patent Application No. 2001-243083, field Aug. 10, 2001, the entire contents of which are incorporated herein by reference.

BACKGROUND OF THE INVENTION

The present invention relates to a water soluble bactericide and a producing method thereof.

The present inventors have long been conducting researches in sterilization using ozone or ozone water. It has been proved through various researches that the strong oxidation ability of ozone is very useful for sterilization. However, depending on a handling manner, ozone is harmful even for the human body and possibly destroys not only bacteria but also cells of the human body, and thus, careful handling is required therefor.

According to the general ozone acquiring method, gas phase oxygen from an oxygen bomb is caused to pass through an ozonizer generating silent discharge under high tension alternating current, thereby to bring material oxygen in contact with the silent discharge field so as to ozonize a portion of the material oxygen. Since the several ten kilovolt high tension alternating current is used for obtaining ozone, a qualified operator is required for operating the ozonizer. Further, since the obtained ozone is in gas phase, handling thereof is difficult so that a special attention is necessary for avoiding any possibility of leakage. Moreover, the thus obtained ozone has a very short half life and thus can not be preserved. Accordingly, it is necessary to bring in an ozonizer equipped with a large-size high voltage power supply device to a using place.

Recently, attention has been paid to liquid phase ozone rather than the foregoing gas phase ozone. This liquid phase ozone is obtained such that a substance having an ozone producing catalyst function, such as gold or platinum, is used as a material of electrodes for electrolyzing water, a portion of oxygen produced through. electrolysis of water is ozonized and the produced ozone is immediately dissolved in water. Therefore, even if this liquid phase ozone leaks, dispersion thereof is limited and thus it is relatively safe. Further, since only ten and several volt dc voltage is sufficient for the electrolysis, the device can be reduced in size, and thus there have already been available an ozone water hand washing apparatus and the like having a high bactericidal efficiency.

However, although using the strong oxidation ability of ozone directly for sterilization as described above is well worth notice, there has been a big question about the safety thereof depending on how to handle it. There has also been a problem in view of the preservability thereof. In general, it is necessary to produce ozone at a using place, which is a main cause of preventing sterilization by ozone from spreading.

SUMMARY OF THE INVENTION

The present invention has been made for solving the foregoing problems. Attention has been paid to the fact that an oxidation effect of ozone on organic matter has a tendency to selectively cleave a specific molecule link portion. Accordingly, researches have been conducted to obtain a substance having a bactericidal ability through oxidation by ozone (hereinafter referred to as "ozone-oxidation"), not using the oxidation ability of ozone directly for sterilization.

Therefore, it is an object of the present invention to provide a water soluble bactericide through ozone-oxidation, which can maintain the oxidation ability over a long term.

According to the first aspect of the present invention, there is provided a water soluble bactericide obtained by oxidizing glycerin with ozone, i.e. by ozone-oxidizing glycerin.

Therefore, hydroxyl group (—OH) of glycerin is selectively oxidized by ozone, so that ozone oxides having oxidation abilities as shown in FIGS. 6 and 7 are produced.

According to the second aspect of the present invention, there is provided a method of producing a water soluble bactericide, wherein liquid phase glycerin and gas phase ozone are brought into gas-liquid contact with each other. In a preferred embodiment, the gas phase ozone is obtained by ozonizing oxygen through contact between oxygen and a silent discharge field.

Therefore, glycerin can be oxidized by ozone (hereinafter referred to as "ozone-oxidized") by simply aerating liquid phase glycerin with gas phase ozone. Ozone has a strong oxidation ability, and thus, heating, agitation or the like is not necessary. Rather than a rapid reaction, a gradual reaction is desirable for the selective oxidation. Since a material of ozone is limited to oxygen, there is no entering of nitrogen oxide which would otherwise enter when air is used as a material, production of a substance associated with nitrogen oxide, which would be otherwise caused following ozone-oxidation, can be prevented.

According to the third aspect of the present invention, there is provided method of producing a water soluble bactericide, wherein a 0.1 to 20% glycerin aqueous solution and gas phase ozone are brought into gas-liquid contact with each other. In a preferred embodiment, the gas phase ozone is obtained by ozonizing oxygen through contact between oxygen and a silent discharge field.

Therefore, since glycerin is in the form of an aqueous solution, the viscosity of glycerin is lowered. Accordingly, the gas-liquid contact can be performed efficiently to achieve ozone-oxidation in a relatively short time. The obtained water soluble bactericide differs in oxidation ability and its half life depending on a glycerin concentration. Thus, the oxidation ability and its half life can be set according to the purpose of its use.

According to the fourth aspect of the present invention, there is provided a method of producing a water soluble bactericide, wherein a glycerin aqueous solution is electrolyzed. In a preferred embodiment, the glycerin aqueous solution is a 0.1 to 20% glycerin aqueous solution. Further, in a preferred embodiment, the glycerin aqueous solution is electrolyzed in an electrolytic device wherein dc voltage is applied across electrodes. Further, in a preferred embodiment, a substance having an ozone producing catalyst function, such as gold, platinum or titanium, is used as a material of electrodes.

Therefore, water is electrolyzed to produce oxygen and a portion thereof is ozonized by the catalyst function of the electrodes, so that ozone thus produced oxidizes glycerin directly or after dissolving in water. In the foregoing method according to the second aspect of the present invention, only the saturation ozone amount which can dissolve in water is utilized. On the other hand, in the method according to the fourth aspect of the present invention, the ozone-oxidation can be theoretically continued until all the added water is electrolyzed.

BRIEF DESCRIPTION OF THE DRAWINGS

The present invention will be understood more fully from the detailed description given hereinbelow, taken in conjunction with the accompanying drawings.

In the drawings.

DESCRIPTION OF THE PREFERRED EMBODIMENT

Now, a preferred embodiment of the present invention, will be described hereinbelow with reference to the accompanying drawings.

In this embodiment, glycerin is first prepared. In this embodiment, glycerin mainly represents concentrated glycerin with 98% or more concentration according to Japan pharmaceutical codex. However, the concentration is not limited thereto as long as glycerin is in the form of liquid, i.e. in liquid phase. This glycerin is ozone-oxidized so as to be a water soluble bactericide.

According to the method of obtaining ozone most easily, an ozone producing device called a silent charge type ozonizer is used, wherein the silent charge field is induced between electrodes (a dielectric made of glass or the like is interposed therebetween) using a high voltage ac power supply, and material oxygen is caused to pass in the silent charge field so that oxygen is ozonized.

The thus obtained ozone is brought in contact with glycerin so that glycerin is ozone-oxidized. In this embodiment, a silent charge type ozonizer having an ozone producing capability of 1.6 g/hour was used, and oxygen was caused to pass through the silent charge type ozonizer at 1 m$^3$/min. Further, the tip of a glass tube with an inner diameter of 3 mm connected to a discharge port of the silent discharge type ozonizer was immersed in concentrated glycerin of 100 g put in a measuring cylinder. Then, ozone in the form of bubbles was introduced into glycerin in the measuring cylinder from the tip of the glass tube so that glycerin and ozone were contacted with each other. In this state, ozone in the form of bubbles was continuously introduced for 3 hours or more, then glycerin was gradually oxidized thereby to become a substance having a bactericidal ability. Ozone-proof Teflon (registered trademark) products were used for hoses and the like of an experimental apparatus.

Figure 1:
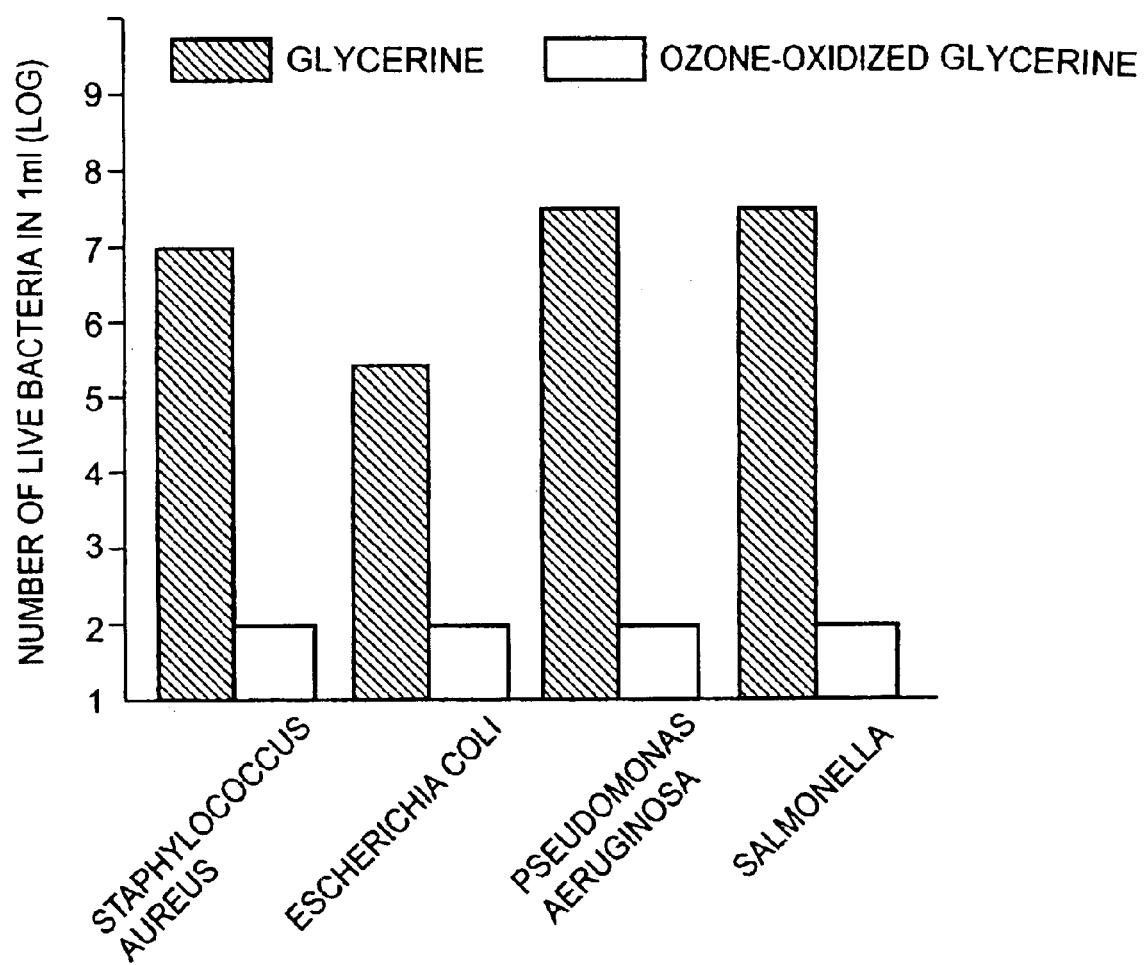
FIG. 1 shows a graph for comparing bactericidal abilities between glycerin and ozone-oxidized glycerin.

The bactericidal ability of the foregoing ozone oxide of glycerin was tested and the result thereof was as follows. As sample fungus bodies, a standard strain of *Staphylococcus aureus*, a standard strain of *Escherichia coli*, a standard strain of *Pseudomonas aeruginosa* and a clinical isolated strain of Salmonella were selected as bacteria causing in-hospital infection or food poisoning. As a culture medium, (nutrient agar flat plate (NA), Muller-Hinton Broth (MHB)) was used. Each cultured fungus (37° C.) was floated in a sterilized physiological salt solution and adjusted to McF NO3 (bacteria concentration index: $9.0 \times 10^8$/ml). Then, lad of ozone-oxidized glycerin and 1 ml of glycerin were measured into sterilized small test tubes, respectively, and fungus liquids each of 100 ml were measured into the respective test tubes and well mixed. 90 ml of MHB was measured into each hole of a 96-hole sterilized plate beforehand, and the prepared test liquids each of 10 ml were measured into the respective holes. Then, the bacteria were cultured overnight in the plate at 37° C., and development of the bacteria was observed. As a result, the bactericidal effects of ozone-oxidized glycerin against the respective strains were higher than those of glycerin as shown in FIG. 1. The bactericidal effects of ozone-oxidized glycerin were recognized immediately after the contact in case of *Escherichia coli* and *Pseudomonas aeruginosa*, while with a lapse of time in case of *Staphylococcus aureus* and Salmonella. Since the bactericidal effects were not recognized in case of glycerin, it is considered that the respective strains were sterilized by ozone-oxidized glycerin.

Figure 2:
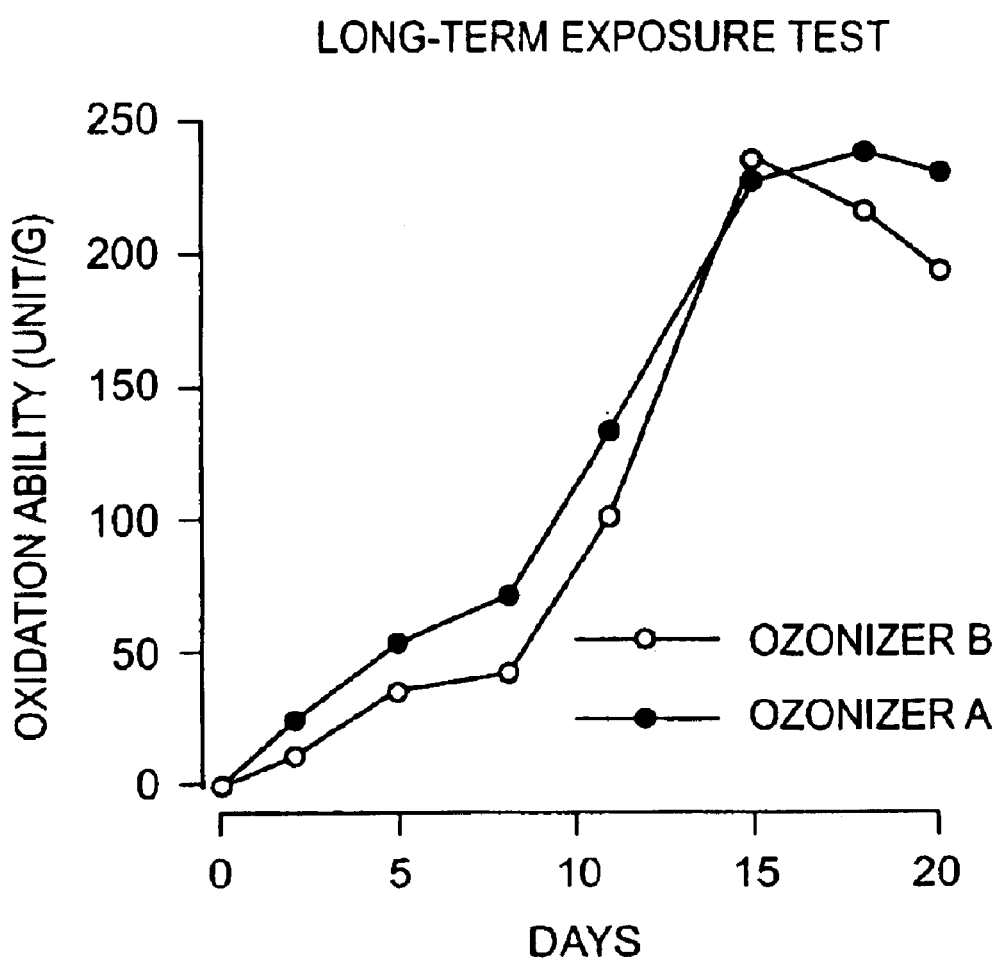
FIG. 2 shows a graph representing the result of a glycerin-ozone long-term exposure test.

It is described above that "ozone in the form of bubbles was continuously introduced for 3 hours or more, then glycerin was gradually oxidized thereby to become a substance having a bactericidal ability". The oxidation of glycerin by ozone is quite gradual. Accordingly, for examining a reaction end point, an ozone gas long-term exposure test was conducted. In the test, two ozonizers A and B having different ozone gas generation efficiencies were used, wherein the ozonizer A had an ozone producing capability of 1.6 g/hour and the ozonizer B had an ozone producing capability of 0.06 g/hour. The result is shown in FIG. 2. In the initial stage (within 7 days), the ozonizer A having a higher ozone gas generation efficiency exhibited a higher oxidation efficiency. On the other hand, both exhibited the maximum oxidation ability (about 200 unit/g: oxidation ability corresponding to about 200 ppm ozone per 1 g of glycerin) in 14–15 days.

In the foregoing bactericidal ability test, the result of which is shown in FIG. 1, ozone-oxidized glycerin exhibiting an oxidation ability of about 10 unit/g (1 unit/g corresponds to 1 ppm ozone) was used.

As a counterargument to the foregoing bactericidal ability of ozone-oxidized glycerin, the following are expected.

Figure 6:
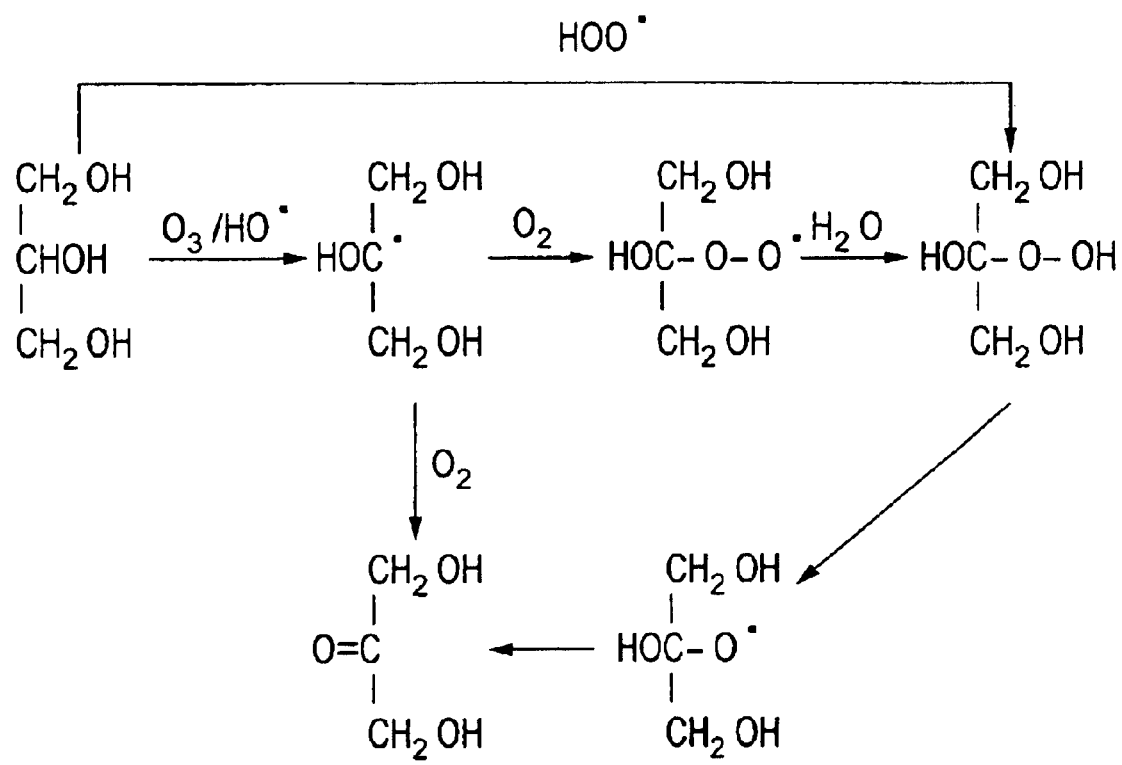
FIG. 6 is a diagram showing molecular structures of ozone-oxidized glycerin according to the present invention.
Figure 7:
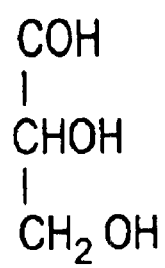
FIG. 7 is a diagram showing molecular structures of ozone-oxidized glycerin according to the present invention.
Figure 7:
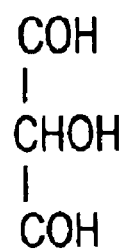
Figure 7:
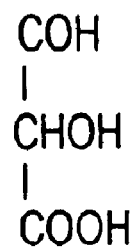
Figure 7:
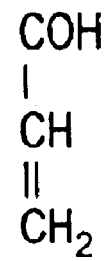
Figure 7:
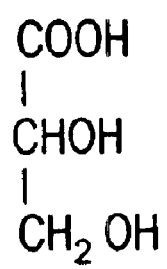
Figure 7:
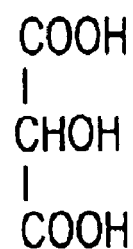
Figure 7:
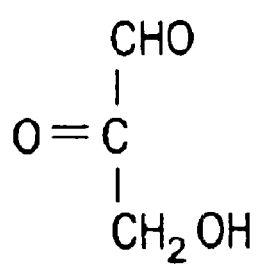
Figure 7:
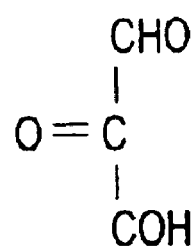
Figure 7:
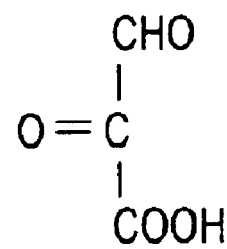
Figure 7:
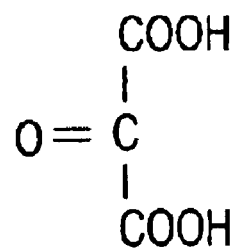

Specifically, (1) hydrogen peroxide may be generated; (2) formaldehyde (formalin: trade name) may be generated; (3) ozone bubbles may be merely mixed in With respect to (1), since catalase being a decomposing enzyme of hydrogen peroxide is reluctant to influence on the oxidation ability of an ozone-oxidized glycerin, the generation of hydrogen peroxide can be denied. With respect to (2), since formaldehyde has approximately no oxidation ability, the generation of formaldehyde can also be denied. With respect to (3), it is considered as follows. Indeed, it can not be denied immediately after the production because there was an odor of ozone. In this regard, since it is acknowledged that a natural half life of ozone is about two hours, a test was conducted in which the assumed ozone-oxidized glycerin was stood still for several days. As a result, the bactericidal ability was hardly lowered. Further, when the assumed ozone-oxidized glycerin was sealed and stood still in the natural state, the oxidation ability was not lowered over 80 days. Thus, the oxidation ability by the ozone bubbles can also be denied. Accordingly, as compounds having the oxidation and bactericidal abilities other than the foregoing (1) to (3), substances as shown in FIG. 6 may be expected. However, since these substances are unstable, it is believed that a possibility is high for them to have advanced to stabler substances as shown in FIG. 7. On the other hand, it can not also be denied that the respective substances shown in FIG. 6 may have some influence on the bactericidal ability. FIGS. 6 and 7 show an assumption of expectable formation of ozone oxides of glycerin and change of molecular structures thereof, for the purpose of assuming structures of ozone-oxidized glycerin.

Figure 8:
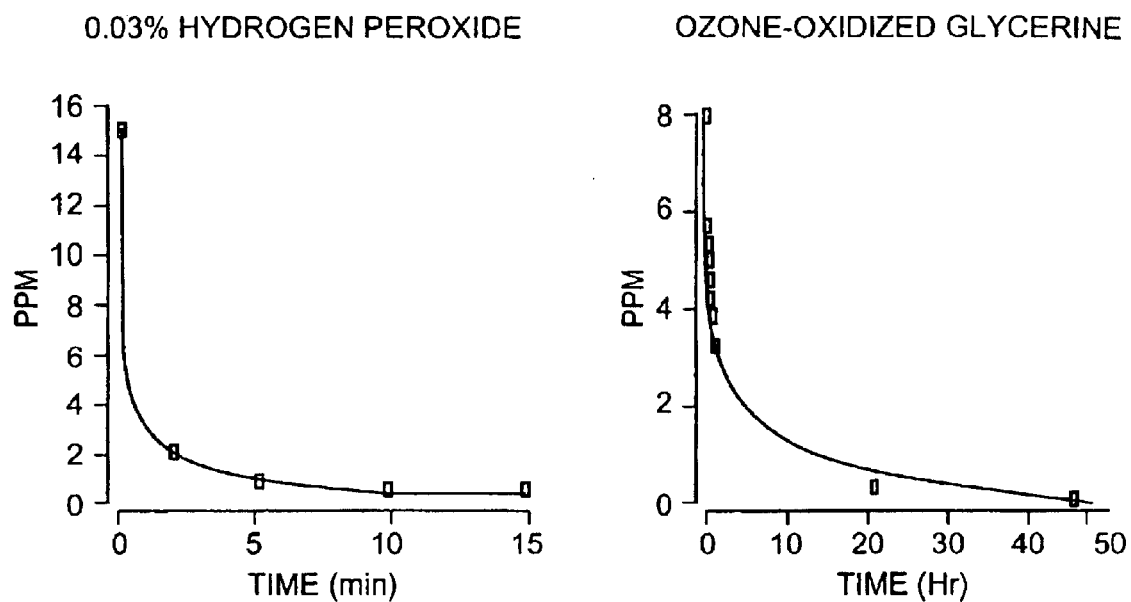
FIG. 8 shows graphs for comparing time dependent attenuation of oxidation abilities between ozone-oxidized glycerin according to the present invention and hydrogen peroxide.

FIG. 8 shows graphs representing results of tests in which catalase being a decomposing enzyme of hydrogen peroxide was used. In FIG. 8, the left-side graph shows the result of the test wherein catalase Was added into 0.03% hydrogen peroxide solution such that the final concentration of catalase became 0.003%, and the right-side graph shows the result of the test wherein catalase was added into ozonized glycerin, i.e. ozone-oxidized glycerin, such that the final concentration of catalase became 0.003%. In each test, the oxidation ability was measured in time sequence using a potassium iodide titration method. In the left-side graph, the axis of abscissas is defined in the unit of minute, while the axis of abscissas is defined in the unit of hour in the right-side graph. As a result, due to the application of catalase, the oxidation ability of 0.03% hydrogen peroxide was rapidly attenuated and almost disappeared in 5 minutes. On the other hand, although the oxidation ability of ozone-oxidized glycerin was also attenuated due to the application of catalase, its speed was very slow so that the oxidation ability was retained even after a lapse of an hour. The oxidation ability disappeared in about 20 hours. Accordingly, it was confirmed that the characteristic of ozone-oxidized glycerin has a durability.

When propylene glycol being a viscous substance lacking one hydroxyl group from glycerin was reacted with ozone in the sane manner as described above, a substance having a similar oxidation ability was produced, which, however, had a bad smell with an odor of acetic acid. On the other hand, the ozone oxide of glycerin slightly had an odor of ozone immediately after the production, but such an odor disappeared in about 10 hours. Accordingly, the bactericide having a wide range of application can be provided, wherein the bactericide can also be used even as a disinfectant for internal use or the like.

Figure 3:
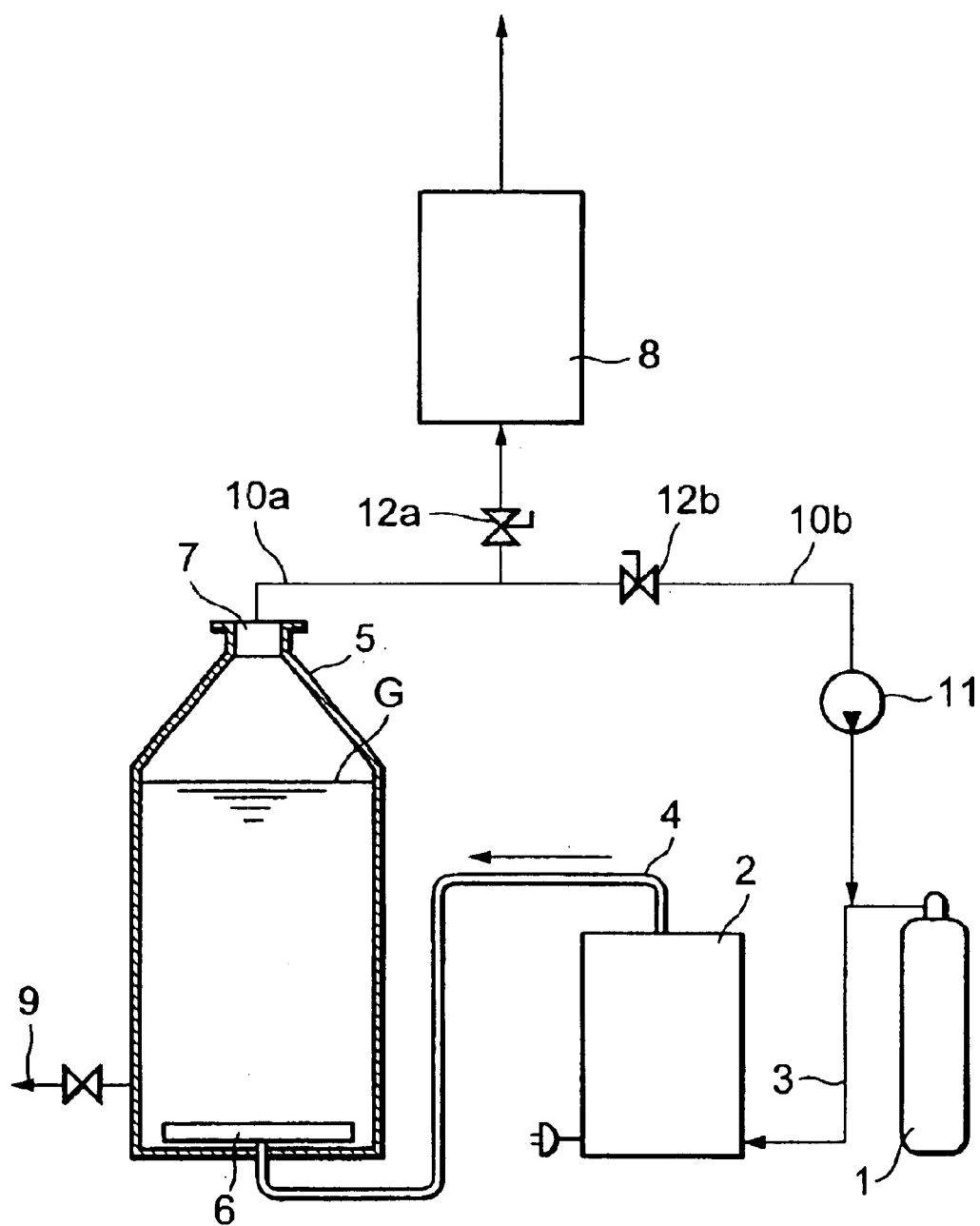
FIG. 3 is a partially sectional front view schematically showing an example of an apparatus for implementing the present invention.

According to example 1 of the present invention, liquid phase glycerin and gas phase ozone obtained by ozonizing oxygen through contact between oxygen and the silent discharge field, are brought into gas-liquid contact with each other. For achieving this gas-liquid contact, as described before, ozone in the form of bubbles is introduced into liquid glycerin from the glass tube. A preferred example of such an apparatus is shown in FIG. 3. In FIG. 3, numeral 1 denotes an oxygen bomb, and numeral 2 denotes a silent discharge type ozonizer. A discharge port of the oxygen bomb 1 and a material inlet of the silent discharge type ozonizer 2 are connected by a connecting tube 3.

A transfer tube 4 extends from a discharge port of the silent discharge type ozonizer 2. The tip of the transfer tube 4 is connected to a filtros plate 6 disposed in a reaction vessel 5. In the reaction vessel 5, liquid phase glycerin G is contained with a predetermined liquid level so that the filtros plate 6 is immersed therein.

In FIG. 3, numeral 7 denotes an exhaust port to which an ozone killer vessel 8 in the form of an activated carbon vessel or the like is connected through an exhaust tube 10a. Exhaust gas discharged from the exhaust port 7 is introduced into the ozone killer vessel 8 where remaining ozone, if any, is restored to oxygen so as to be discharged. In the figure, numeral 9 denotes a product take-out opening. Numeral 10b denotes an exhaust gas circulation passage provided with a pump 11. An upstream end of the exhaust gas circulation passage is connected to the exhaust tube 10a in a branching manner between the exhaust port 7 and the ozone killer vessel 8, and a downstream end thereof is connected to the material inlet of the silent discharge type ozonizer 2. A valve 12a is provided in the exhaust tube 10a downstream of the junction between the exhaust tube 10a and the exhaust gas circulation passage 10b, and a valve 12b is provided in the exhaust gas circulation passage 10b. With this arrangement, depending on opening/closing states of the valves 12a and 12b, selection can be made between a case in which exhaust gas is discharged to the air via the ozone killer vessel 8 and a case in which exhaust gas is circulated for reuse.

According to example 2 of the present invention, liquid phase glycerin and gas phase ozone obtained by ozonizing oxygen through contact between oxygen and the silent discharge field, are brought into gas-liquid contact with each other for more than several ten hours. As shown in FIG. 2, ozone-oxidation of glycerin advances quite gradually such that the reaction end point is reached after a lapse of several ten hours (in FIG. 2, 15 (days)×24 (hours)=360 (hours)).

According to example 3 of the present invention, a 0.1 to 20% glycerin aqueous solution and gas phase ozone obtained by ozonizing oxygen through contact between oxygen and the silent discharge field, are brought into gas-liquid contact with each other. Although the water soluble bactericide obtained in example 2 has a strong bactericidal ability, the production thereof requires much time and, depending on the purpose of its use, it possibly has an excessive bactericidal ability (oxidation ability).

Figure 12:
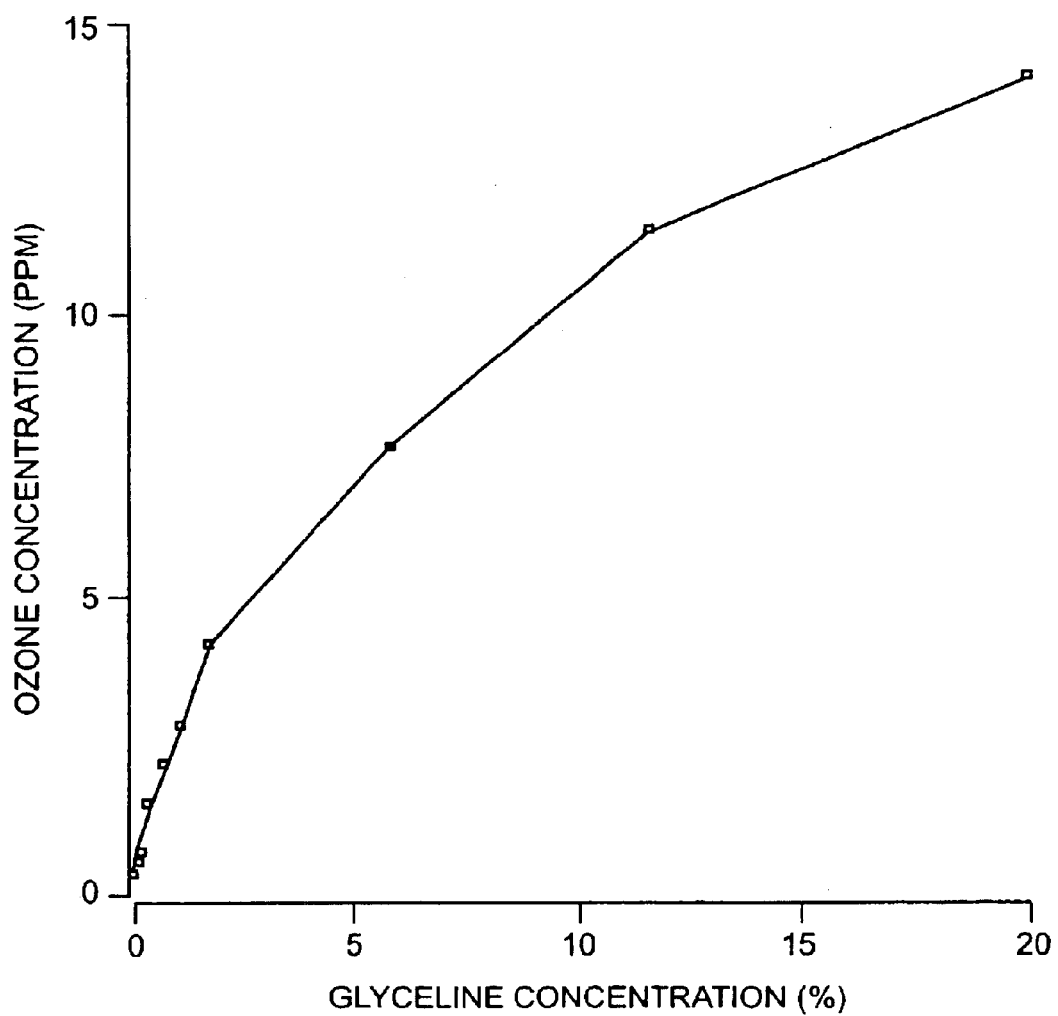
FIG. 12 shows a graph representing oxidation abilities when glycerin aqueous solutions of various concentrations are used as materials.

Therefore, aqueous solutions having different glycerin concentrations were ozone-oxidized, and the result is shown. FIG. 12. In FIG. 12, the axis of abscissas represents glycerin concentrations, while the axis of ordinates represents oxidation abilities obtained by ozone-oxidizing 0.1 to 20% glycerin aqueous solutions. The ozone-oxidation was almost completed in 20 to 40 hours and the oxidation abilities achieved on that occasion were as shown in FIG. 12. A relationship between the glycerin concentrations and the oxidation abilities was as shown in FIG. 12, wherein in case of a 20% glycerin aqueous solution, the oxidation ability of 13.61 ppm was exhibited, in case of a 10% glycerin aqueous solution, 10.98 ppm, in case of a 5% glycerin aqueous solution, 8.33 ppm, in case of a 2.5% glycerin aqueous solution, 5.54 ppm, in case of a 1.25% glycerin aqueous solution, 3.89 ppm, in case of a 0.63% glycerin aqueous solution, 2.89 ppm, in case of a 0.31% glycerin aqueous solution, 2.11 ppm, in case of a 0.16% glycerin aqueous solution, 1.27 ppm, in case of a 0.08% glycerin aqueous solution, 0.86 ppm, in case of a 0.04% glycerin aqueous solution, 0.60 ppm, and in case of a 0.02% glycerin aqueous solution, 0.59 ppm. Ozone-oxidized glycerin based on the 5% or more glycerin aqueous solution is suitable for sterilizing medical appliances and the like, ozone-oxidized glycerin based on the about 1% glycerin aqueous solution is suitable for disinfecting floors, hand washing and the like, and ozone-oxidized glycerin based on the about 0.15% glycerin aqueous solution is suitable for spray sterilization in rooms and the like.

Figure 9:
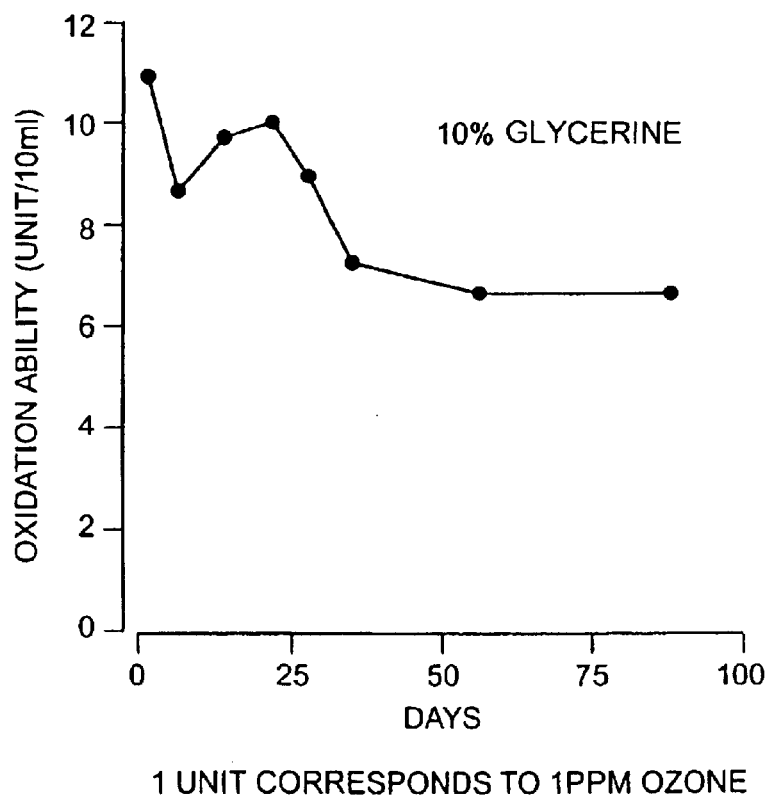
FIG. 9 shows a graph representing time dependent attenuation of oxidation abilities when a 10% glycerin aqueous solution is used as a material.
Figure 10:
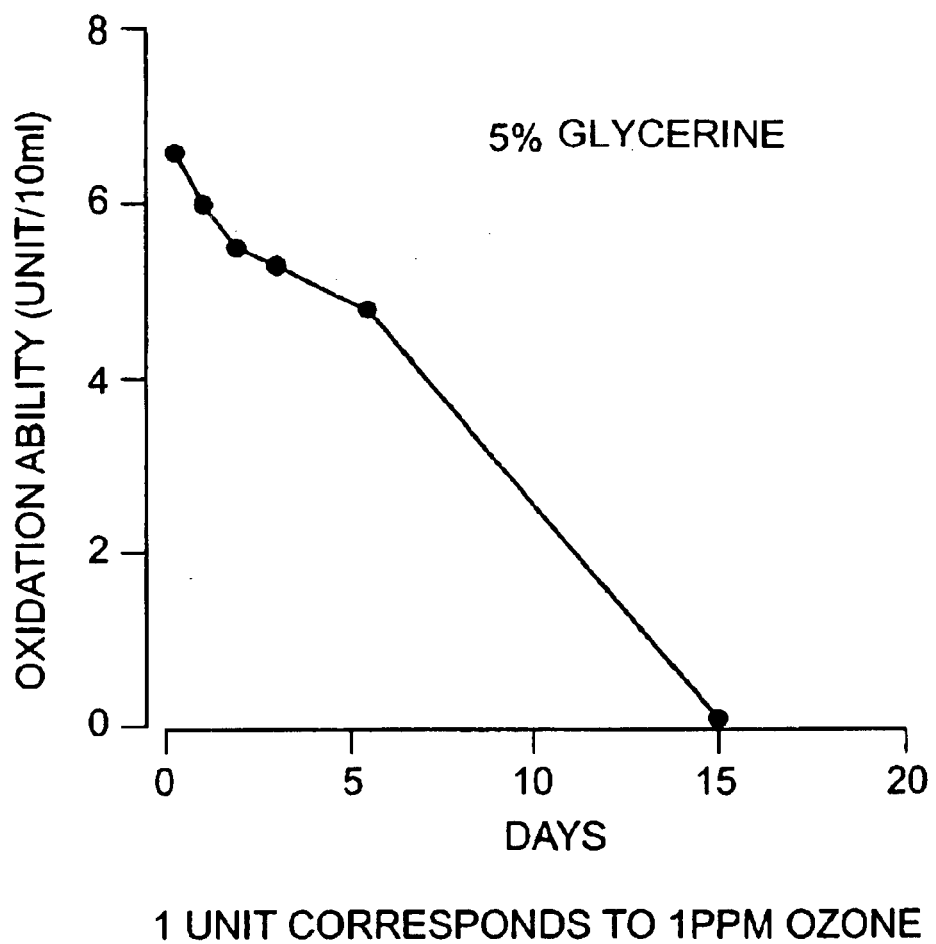
FIG. 10 shows a graph representing time dependent attenuation of oxidation abilities when a 5% glycerin aqueous solution is used as a material.
Figure 11:
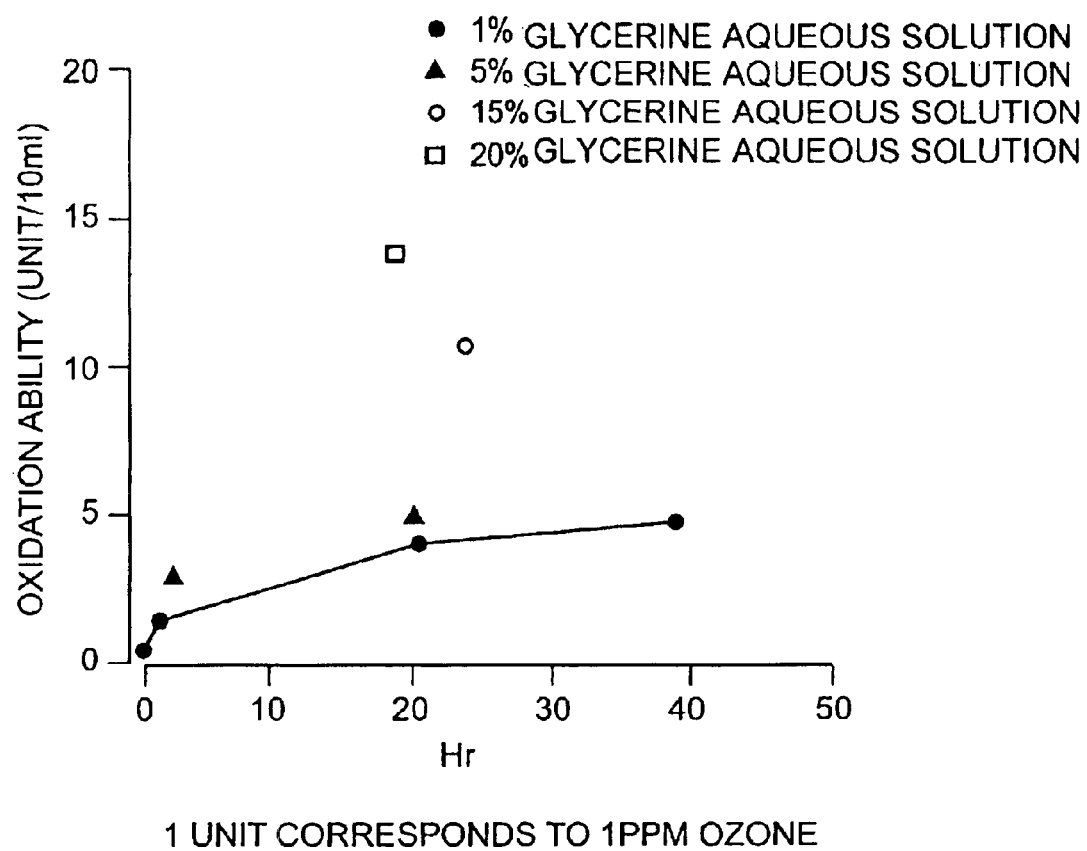
FIG. 11 shows a graph representing ozone-oxidation speeds when glycerin aqueous solutions of various concentrations are used as materials.

A half life (preservability) of the oxidation ability is influenced by the glycerin concentration. FIG. 9 shows a case in which a 10% glycerin aqueous solution was ozone-oxidized, wherein the oxidation ability was stable for about 3 months or longer. On the other hand, as shown in FIG. 10 wherein a 5% glycerin aqueous solution was ozone-oxidized, the oxidation ability was stable for about one week, but then was rapidly attenuated. This rapid attenuation of the oxidation ability preferably serves to suppress production of carcinogenic substances or lipid peroxide which would be otherwise produced due to sterilization on foods, mucous membrane of the human body or the like.

According to example 4 of the present invention, a 0.1 to 20% glycerin aqueous solution is electrolyzed in an electrolytic device wherein dc voltage is applied across electrodes having an ozone producing catalyst function. According to examples 1 to 3, glycerin is ozone-oxidized by contacting gas phase ozone with glycerin. However, in this case, although the produced substance can be fully used as a bactericide, reaction requires much time and there is a concern about leakage of gas phase ozone during the production process. Accordingly, in this example, an electrolytic ozonizer is used, thereby to efficiently implement ozone-oxidation with no concern about leakage of ozone.

Figure 4:
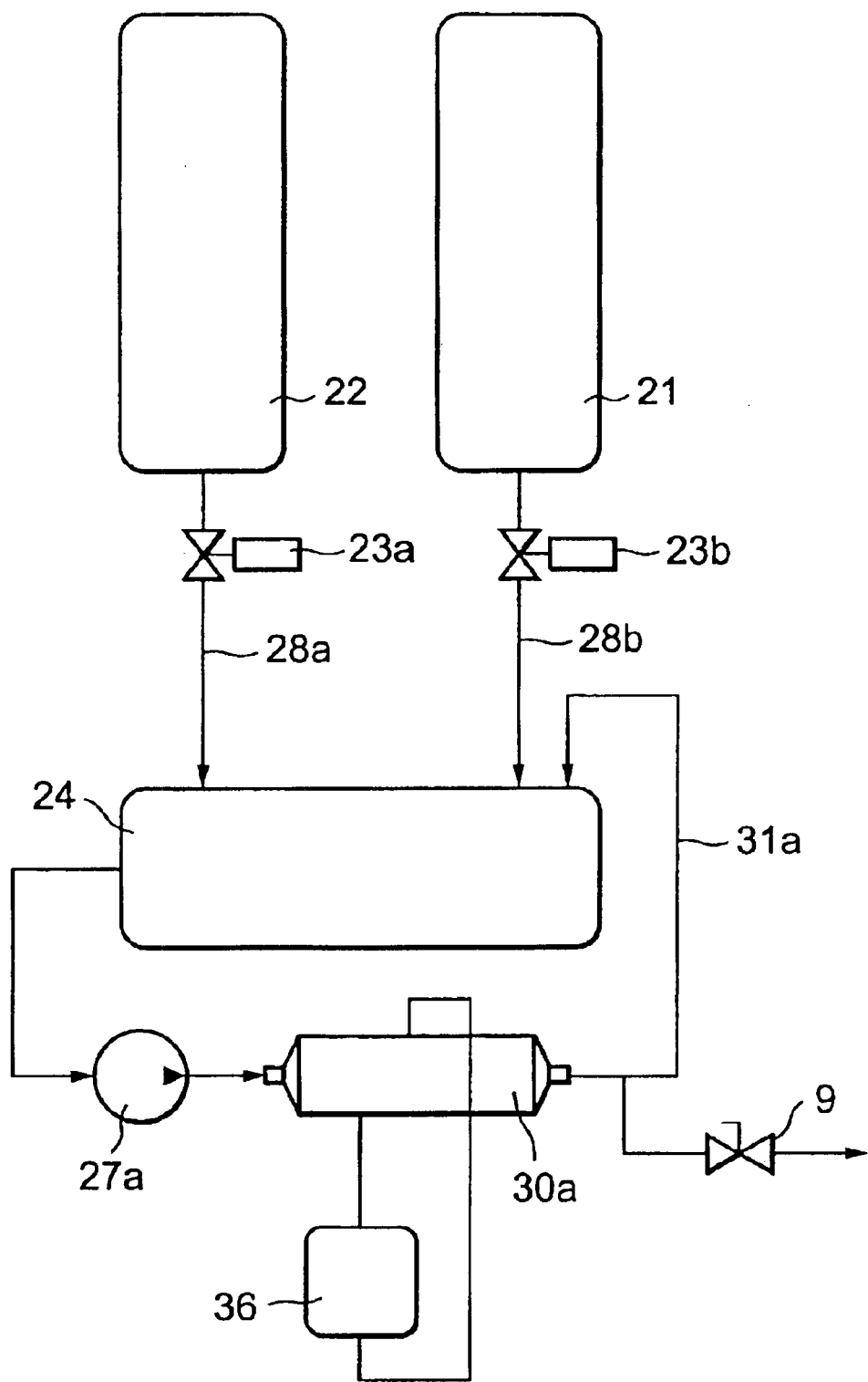
FIG. 4 is a front view schematically showing another example of an apparatus for implementing the present invention.
Figure 5:
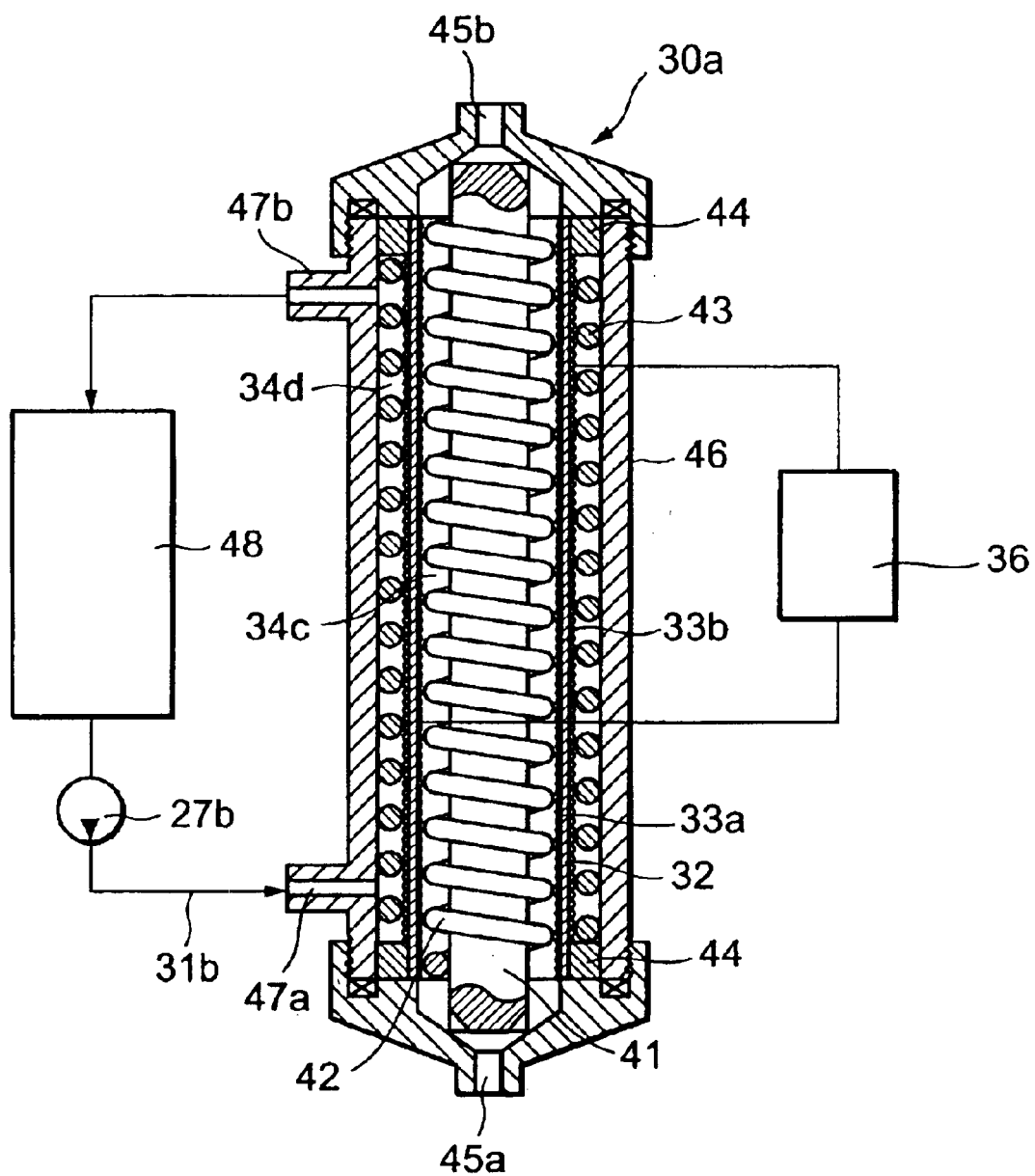
FIG. 5 is a sectional view showing an ozonizer incorporated in the apparatus shown in FIG. 4.

This example aims to carry out ozone-oxidation to a sufficient level with a predetermined amount of water. FIGS. 4 and 5 show a preferred example of an apparatus for implementing the present invention. The apparatus comprises a water tank 21, a glycerin tank 22, valves 23a and 23b, discharge passages 28a and 28b, and a mixing chamber 24. A circulation passage 31a provided with a circulation pump 27a is connected to the mixing chamber 24. Further, an electrolytic ozonizer 30a is interposed on the midway of the circulation passage 31a.

As shown in FIG. 5, the electrolytic ozonizer 30a has a cylindrical or tubular shape with an ion exchange membrane 32 being wound around in a tubular shape for the sake of convenience in production. In the electrolytic ozonizer 30a, a spacer 42 is helically wound around a cylindrical core 41 and, on the outer side of the spacer 42, an anode electrode 33a, the ion exchange membrane 32 and a cathode electrode 38b are wound around in the order named. A dc power supply 36 is connected between the anode electrode 33a and the cathode electrode 33b, thereby to apply dc voltage therebetween. A 15 cm² Naphyon 450 (trade name) is used for the ion exchange membrane 32, and a 55-mesh wire net made of platinum is used for each of the anode electrode 33a and the cathode electrode 33b.

A spacer 43 is further wound helically around the cathtode electrode 33b, and the unit of the core 41, the spacer 42, the anode electrode 33a, the ion exchange membrane 32, the cathode electrode 33b and the spacer 43 is press-fitted into an outer tube 46. Seal rings 44, 44 are disposed to seal a space between the ion exchange membrane 32 and the outer tube 46 at both axial or longitudinal ends thereof. The outer tube 46 is provided with an inlet 45a and an outlet 45b at both longitudinal ends thereof. A helical flow passage 34c is formed by the spacer 42 and interposed on the midway of the circulation passage 31a (see FIG. 4) so as to form a portion of the circulation passage 31a.

The outer tube 46 is provided on the outer periphery thereof with an inlet 47a at one longitudinal end thereof, and with an outlet 47b at the other longitudinal end thereof. The inlet 47a communicates with one end of a helical space 34d formed by the spacer 43, while the outlet 47b communicates with the other end of the helical space 34d. The inlet 47a and the outlet 47b are connected to each other via a circulation passage 31b which is provided with a tank 48 and a pump 27b on the midway thereof. In the tank 48, as wash water for the cathode electrode 33b, an electrolytic solution (for example, sodium chloride or sodium citrate mixture aqueous solution) having a 300 μs□cm or greater conductivity is contained. By using this wash water, calcium ions and magnesium ions are liable to be emitted into the wash water from the ion exchange membrane 32, so that contamination of the electrode can be suppressed even when the apparatus is continuously operated.

According to the foregoing embodiment and examples, a water soluble bactericide which is almost tasteless and odorless can be obtained. As described above, the obtained ozone-oxidized glycerin is a persistent oxide and thus can maintain the bactericidal ability over a long term.

While the present invention has been described in terms of the preferred embodiment and examples, the invention is not to be limited thereto, but can be embodied in various ways without departing from the principle of the invention as defined in the appended claims.

What is claimed is:

1. A method of producing a water soluble bactericide, wherein liquid phase glycerin in the form of a 0.1 to 20% glycerin aqueous solution and gas phase ozone obtained by ozonizing oxygen through contact between oxygen and a silent discharge field are brought into gas-liquid contact with each other and wherein the glycerin aqueous solution is electrolyzed.

* * * * *